(12) United States Patent
Hahnl et al.

(10) Patent No.: US 11,660,459 B2
(45) Date of Patent: May 30, 2023

(54) TREATMENT ARRANGEMENT, METHOD FOR PRODUCING A TREATMENT ARRANGEMENT

(71) Applicant: CINOGY GMBH, Duderstadt (DE)

(72) Inventors: Mirko Hahnl, Berlingerode (DE);
Leonhard Trutwig, Duderstadt/Gerlingerode (DE);
Karl-Otto Storck, Duderstadt (DE);
Dirk Wandke, Heilbad Heiligenstadt (DE)

(73) Assignee: CINOGY, Duderstadt (DE)

( * ) Notice: Subject to any disclaimer, the term of this patent is extended or adjusted under 35 U.S.C. 154(b) by 1188 days.

(21) Appl. No.: 16/095,118

(22) PCT Filed: Feb. 17, 2017

(86) PCT No.: PCT/DE2017/100138
§ 371 (c)(1),
(2) Date: Oct. 19, 2018

(87) PCT Pub. No.: WO2017/190724
PCT Pub. Date: Nov. 9, 2017

(65) Prior Publication Data
US 2019/0308027 A1    Oct. 10, 2019

(30) Foreign Application Priority Data
May 6, 2016 (DE) .................. 10 2016 108 450.6

(51) Int. Cl.
*A61N 1/44* (2006.01)
*A61F 13/00* (2006.01)
(Continued)

(52) U.S. Cl.
CPC .......... *A61N 1/44* (2013.01); *A61F 13/00051* (2013.01); *A61N 1/0468* (2013.01);
(Continued)

(58) Field of Classification Search
CPC ................ A61N 1/44; A61N 1/0468
(Continued)

(56) References Cited

U.S. PATENT DOCUMENTS

| 2012/0213664 | A1* | 8/2012 | Diver ............. | A61L 2/202 422/22 |
| 2016/0045246 | A1 | 2/2016 | Stieber et al. | |
| 2018/0295708 | A1* | 10/2018 | Trutwig ........... | H05H 1/2406 |

FOREIGN PATENT DOCUMENTS

| WO | 2012/106735 A2 | 8/2012 |
| WO | 2013/040542 A1 | 3/2013 |

* cited by examiner

*Primary Examiner* — Nicole F Lavert
(74) *Attorney, Agent, or Firm* — WCF IP

(57) ABSTRACT

In a treatment arrangement for treating a surface, with a planar electrode array (2,2'), to which an electrical voltage can be fed, and with a planar shielding layer (1) which is made of an insulating plastic and which ate least partially surrounds the electrode array (2,2'), a reliable and fixed connection between the electrode array (2,2') and shielding layer (1) is achieved by the fact that electrode array (2,2') is made of a pourable plastic provided with plastic additives and that, in the region of a boundary layer (22) between electrode array (2,2') and shielding layer (1), the plastics of the electrode array (2,2') and of the shielding layer (1) are connected to each other by material bonding.

18 Claims, 6 Drawing Sheets

(51) Int. Cl.
 *A61N 1/04* (2006.01)
 *H05H 1/24* (2006.01)
 *A61N 1/40* (2006.01)
(52) U.S. Cl.
 CPC .............. *A61N 1/0492* (2013.01); *A61N 1/40* (2013.01); *H05H 1/2406* (2013.01); *H05H 1/2418* (2021.05); *H05H 2277/10* (2013.01)
(58) Field of Classification Search
 USPC .......................................................... 604/20
 See application file for complete search history.

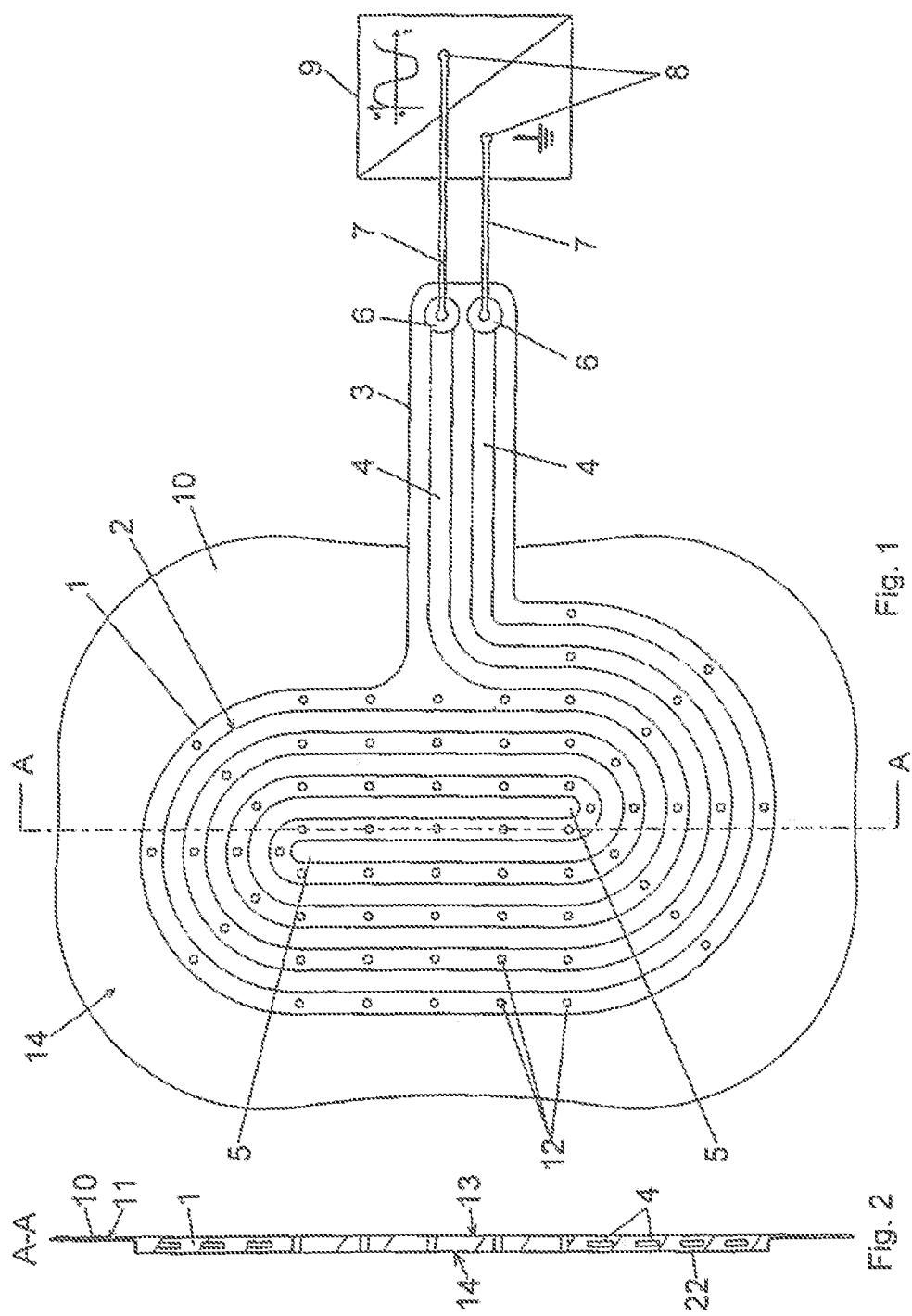

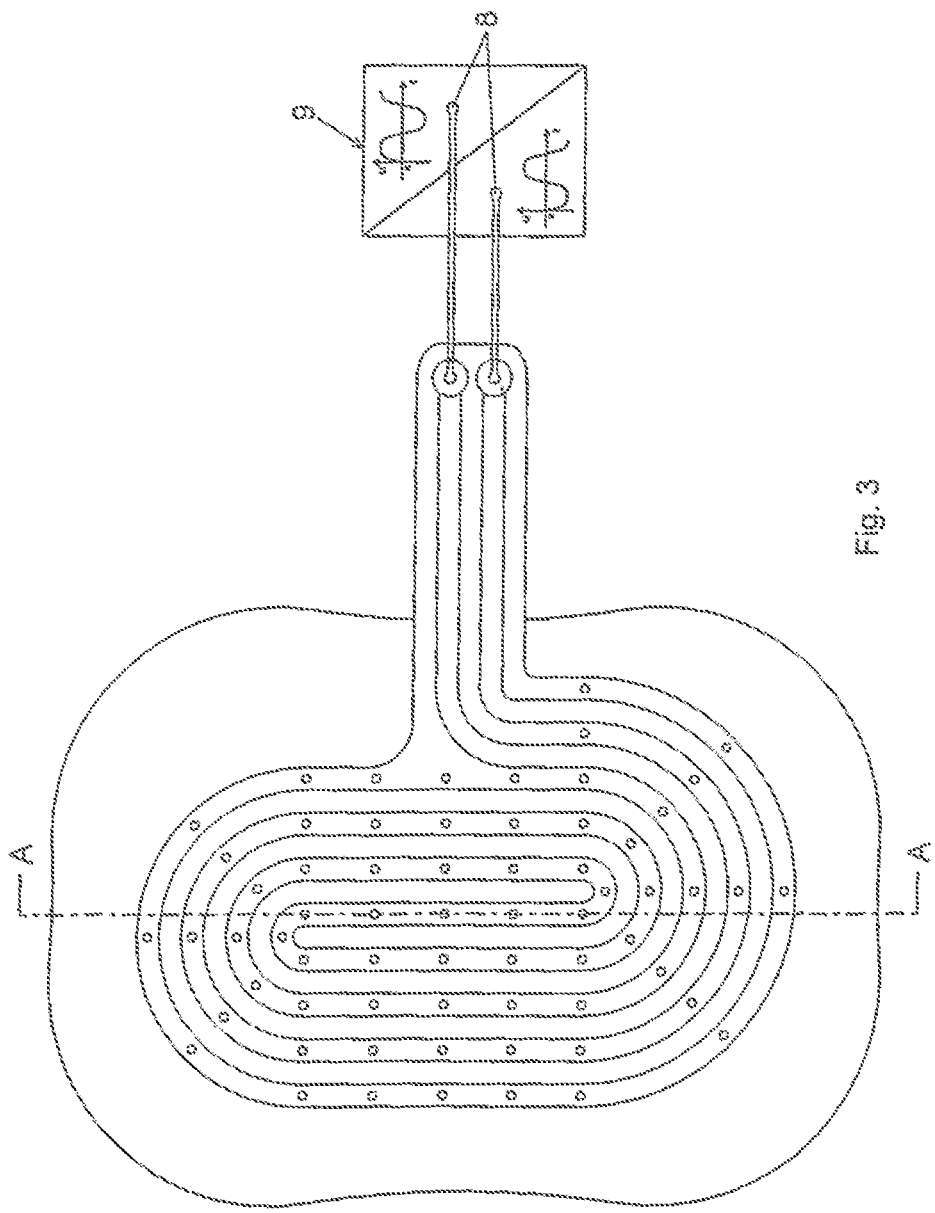

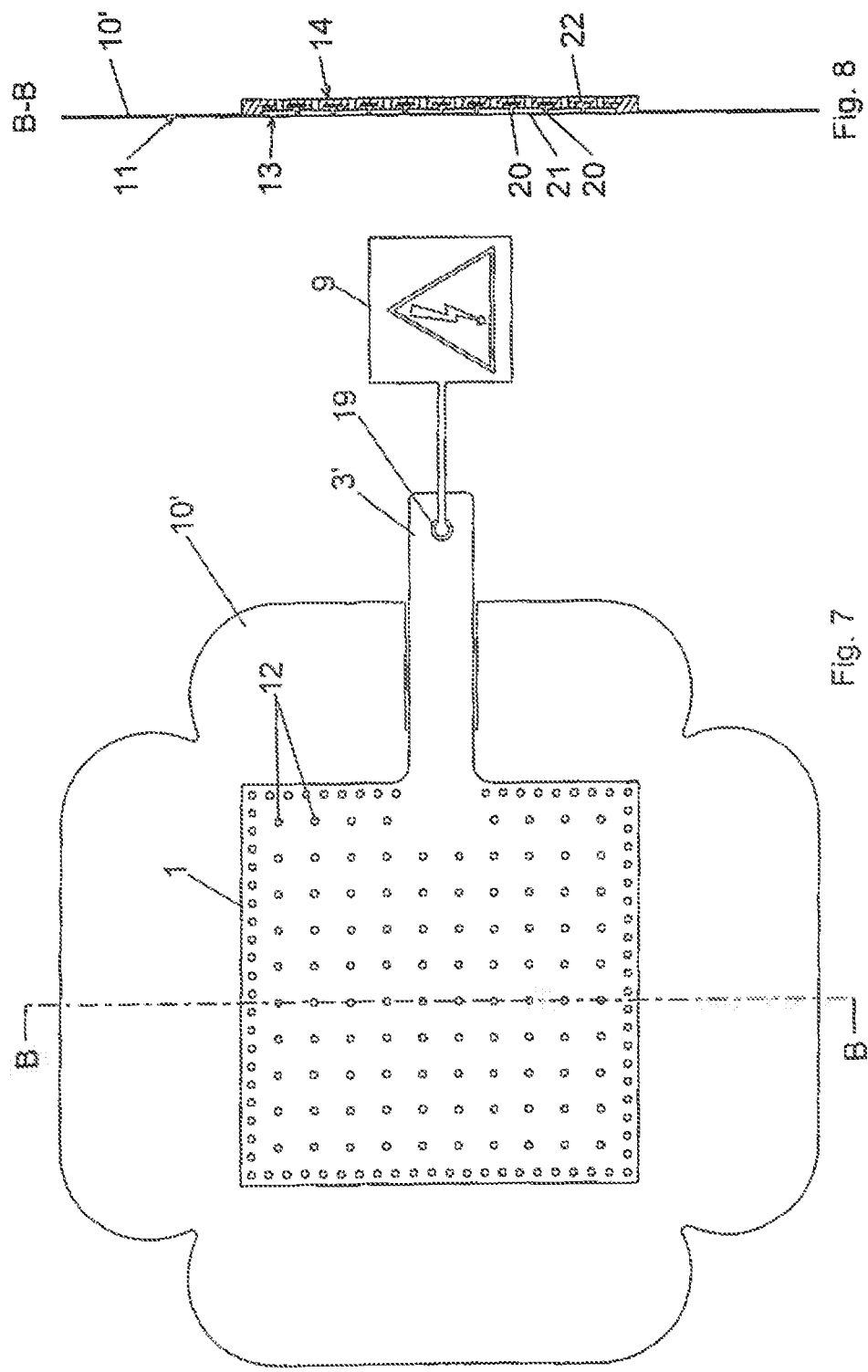

TREATMENT ARRANGEMENT, METHOD FOR PRODUCING A TREATMENT ARRANGEMENT

FIELD OF THE INVENTION

The invention relates to a treatment arrangement for treating a surface, comprising a planar electrode arrangement, to which an electric voltage can be supplied, and a planar shielding layer consisting of an insulating plastic, which at least partially encloses the electrode arrangement.

The invention furthermore relates to a treatment device comprising such a treatment arrangement and a method for producing a treatment arrangement of the mentioned type.

BACKGROUND

Various treatment arrangements are known, using which a surface can be treated under the action of electrical voltages. These include treatment arrangements in which a current is introduced directly into the surface to be treated. The shielding layer has the function in this case of avoiding touching of the electrode by an operator.

Furthermore, performing inductive heating of the surface to be treated by means of the electrode is known. In this case, the shielding layer is used to insulate the electrode in relation to the surface to be treated, to prevent a direct current introduction and possibly the formation of flashover sparks.

SUMMARY

In one preferred embodiment of the treatment arrangement according to the invention, it is designed as a plasma treatment device and is used to build up a high-voltage field by means of the electrode arrangement by ionizing an air space or gas space between the treatment arrangement and the surface to be treated to form a plasma, and therefore a plasma treatment of the surface known per se takes place. In this case, in the scope of the present invention, the electrode arrangement can be connected to a pole of an electric voltage and the surface to be treated can form a counter electrode. However, it is also possible to form the electrode arrangement from at least two electrodes, which are connected to different poles of an electric voltage, and therefore an electric field is built up between the electrodes, using which, for example, air can be ionized to form a plasma.

The surface to be treated can be a material which is prepared on its surface by the treatment, for example, a plasma treatment, for the purpose of being provided with a layer, for example, a protective layer. The treatment of the surface is used for the purpose of improving the adhesion of the layer like a primer treatment. Such treatments come into consideration for materials made of plastic, metal, wood, or the like.

One preferred application in the scope of the invention is the treatment of human or animal skin as the surface to be treated. In particular for the formation of a plasma, advantageous effects on the skin surface have been proven. In particular, the plasma treatment has a disinfecting, i.e., germ-killing effect. Designing a treatment arrangement for a plasma treatment in the form of a wound dressing is therefore known. The layer of the treatment arrangement facing toward the wound can be formed in this case from silicone, which is known to be skin-friendly and skin-compatible and is suitable as an insulating layer. One material coming into consideration is, for example, the silicone gel SILPURAN® from Wacker Chemie AG, Burghausen, Germany. This two-component silicone gel crosslinks to form a soft silicone layer which has a certain stickiness and therefore adheres to the skin.

Forms of such treatment arrangements coming into consideration are known, for ex ample, from DE 10 2014 013 716 A1 and are known for the treatment of skin and/or of wounds using a dielectric barrier plasma. In this case, a metallic electrode is completely embedded in a dielectric material, which can be a silicone. To enable the drainage of wound secretions, the dielectric material can be provided with passage openings, through which wound secretions can pass from the wound side of the treatment arrangement to the distal side, where it can be absorbed by an absorption material, for example. The embedded electrode has to be provided in this case with corresponding passage openings, the diameter of which is larger, however, than the diameter of the passage openings in the dielectric material, and therefore the dielectric material also reliably covers the electrode in the region of the channels formed by the passage openings. The electrode embedded in the dielectric material is formed planar, flexible, and monopolar in this case, and therefore the body associated with the skin surface functions as the counter electrode. The counter electrode can be grounded in this case or act as a "floating electrode". The construction of the known treatment arrangements has proven itself, since both the dielectric material and also the electrode itself can be formed as flexible and therefore the entire treatment arrangement is suitable for adapting itself to the possibly irregular shape of a body part and thus carrying out the treatment of an intact skin surface or a wound with defined distance relationships and thus reproducible results.

The present invention is based on the object of simplifying the construction of a treatment arrangement of the type mentioned at the outset and making it even more reliable.

To achieve this object, a treatment arrangement of the type mentioned at the outset is characterized according to the invention in that the electrode arrangement consists of a pourable plastic provided with conductive additives, and in that, in the region of a boundary layer between electrode arrangement and shielding layer, the plastics of the electrode arrangement and the shielding layer are connected to one another by material-to-material joint.

In the treatment arrangement according to the invention, an electrode at least partially enclosed, in particular completely embedded, by the dielectric plastic layer is thus not a metallic electrode, but rather the electrode is itself formed from a suitable plastic, which is made conductive by additives. Such electrodes are known per se. According to the invention, they are used to form the treatment arrangement, in order to thus enable a material-to-material joined connection between the electrode arrangement and the shielding layer, which results due to the plastics themselves and does not have an additional adhesive layer at the boundary layer between the electrode arrangement and the shielding layer. Electrode arrangement and shielding layer can thus be formed as a quasi-unified material and thus ensure a high level of security against delamination of the electrode arrangement from the shielding layer. This is significant in particular if the treatment arrangement is advantageously flexible and enables strong bends, to be able to adapt itself even to difficult body parts, i.e., for example, be able to wrap around a wrist.

The material-to-material joined connection according to the invention between the plastic of the electrode arrangement and the plastic of the shielding layer takes place after mixing of these plastics at least in the region of the boundary layer in a simple manner when the plastics jointly cure and/or crosslink at least in this region. In a further preferred embodiment, chemically identical plastics are used for the electrode arrangement and the shielding layer, which may thus be mixed well. For the electrode arrangement, the plastic is solely provided with the conductive additives in this case, which can be metallic particles, for example, microparticles or nanoparticles, graphite powder, inter alia.

Alternatively, it is possible to dispense with the mixing of the plastics and to produce the positive material joint in that the plastics of electrode arrangement and shielding layer, which abut one another in the boundary layer, crosslink with one another. This can take place in that a first of the plastics is initially only partially crosslinked and is further crosslinked with the second of the plastics during the crosslinking thereof in the meaning of the original crosslinking. In another embodiment, the first of the plastics can also be completely crosslinked if it has functionally crosslinkable peripheral groups, which, upon the supply of the non-crosslinked second of the plastics, during the crosslinking thereof, result in secondary crosslinking between the first plastic and the second plastic.

In one preferred embodiment of the invention, the electrode arrangement is enclosed on all sides by the shielding layer. This is advantageous in particular if a high voltage is supplied to the electrode, as is the case for the treatment using a dielectric barrier plasma in one preferred embodiment of the invention.

In this configuration, it is possible to lead an electrically conductive terminal of the electrode arrangement out of the shielding layer. Alternatively, it is possible to form the electrode arrangement, for example, having a terminal tongue, which is also enclosed by the shielding layer, and to supply the electric voltage using a contact arrangement, which pierces the shielding layer and thus establishes the contact to the electrode arrangement. Such contacting using a self-cutting contact is known, for example, from EP 2 723 447 B1.

It can also be expedient for the treatment arrangement according to the invention if the shielding layer is profiled on the treatment side to form application faces, between which the air intermediate spaces exist to form the plasma upon abutment of the treatment arrangement to the surface to be treated. In this case, the profile can be irregular or regular. A profile in the form of round nubs is known from EP 2 515 997 A1; also a profile in the form of chambers open on one side is known from DE 10 2013 019 057 A1, which are formed on the treatment side of the shielding layer and can optionally be filled with conditioning or healing substances.

For the application as a wound treatment arrangement, it is expedient if a wound dressing surface is formed on the treatment side. This can be formed by the suitable material of the shielding layer itself or can be additionally applied on the treatment side of the shielding layer.

In particular silicones in any form, preferably in the form of silicone gels, are suitable for the shielding layer and the electrode arrangement.

In particular for the purpose of wound care, an embodiment of the treatment arrangement according to the invention is suitable in which the shielding layer has sections protruding beyond the area of the electrode, which are formed as adhesive toward the surface to be treated. The adhesive property of a silicone gel itself can possibly be utilized for this purpose. In this case, the silicone layer can already cause the fastening of the entire arrangement on the skin in the surroundings of the wound, and therefore possibly a secondary bandage in addition to the treatment arrangement can be omitted.

A monopolar electrode can be used as the electrode arrangement of a treatment arrangement according to the invention if the surface to be treated or the body located behind it functions as the counter electrode. Alternatively, the electrode arrangement can be formed as at least bipolar, wherein the two poles are connected to the poles of a voltage supply. The electrodes are then expediently formed and positioned such that the electrode of one pole extends close and parallel to the electrode of the other pole over the area of the treatment arrangement in many regions, and therefore a spatial electrical field suitable for plasma formation arises between these two poles. In order that the electric field is distributed over the area and is not only locally present, the two electrode poles are preferably formed in strips and led parallel or antiparallel over the area of the treatment arrangement, Meandering shapes, spiral courses, comb-shaped structures, etc. are suitable for this purpose.

Using a treatment arrangement according to the invention, a treatment device is preferably formed, which is formed and positioned to change a direct contact of the electrode arrangement and the surface to be treated. As already explained, in particular for a dielectric barrier plasma treatment, embedding the electrode arrangement completely in the electrical shielding layer can suggest itself.

The production of the material bond according to the invention between the plastic of the electrode arrangement and the plastic of the shielding layer is achieved in that, at least in the region of a boundary surface between the electrode arrangement and the shielding layer, the plastics are mixed with one another in a liquid state and jointly cured and/or crosslinked. In this manner, the material bond is caused by a uniform matrix structure or a gradual transition from one matrix structure to the other matrix structure.

It is entirely possible to prefinish the electrode arrangement and/or the shielding layer and partially or entirely crosslink or cure them and subsequently liquefy or at least swell them in the region of a boundary surface, to thus achieve common curing and/or crosslinking in this region.

However, it is preferable for at least one layer of the shielding layer and then the plastic of the electrode arrangement provided with the conductive additives, each in the liquid state, to initially be introduced into a casting mold, such that mixing results in the boundary region between the plastics, and subsequently the plastics are jointly cured and/or crosslinked by cooling. In this case, the possible crosslinking, for example, in the case of a silicone gel, can be carried out by a crosslinking component, which results in the crosslinking in a temperature-dependent or temperature-independent manner.

The mixing of the plastics in the boundary region can be dispensed with in the case of the crosslinking of the plastics with one another. For this purpose, it can be provided that the electrode arrangement or the shielding layer is firstly molded and partially crosslinked using the plastic. The other plastic can then be injected into a mold, for example, an injection mold, and caused to crosslink, wherein the second plastic is selected such that the first plastic, which is initially only partially crosslinked, is further crosslinked at the same time.

Alternatively thereto, it is possible to crosslink the first plastic practically completely and at the same time to provide it with functional, crosslinkable groups. In this case, the first plastic can be laid as a pre-molded part in an injection mold, using which the molding of the second plastic is carried out, which is supplied in the non-crosslinked liquid state. The second plastic is selected in this case such that it produces a secondary crosslinking with the crosslinkable groups of the first plastic part. In particular in the case of silicones, this is possible by OH groups, which enable a polycondensation reaction with cleavage of water. Another example results with remaining reactive SiH groups, which enable additive crosslinking with reactive vinyl groups of the other silicone plastic. However, all other polymerization reactions are also suitable for the secondary crosslinking.

DESCRIPTION OF THE DRAWINGS

The invention will be explained in greater detail hereafter on the basis of exemplary embodiments illustrated in the drawing. In the figures:

FIG. 1—shows a top view of a first exemplary embodiment of a treatment arrangement according to the invention, which is connected to a voltage supply device;

FIG. 2—shows a section through the treatment arrangement according to FIG. 1 along line A-A;

FIG. 3—shows the exemplary embodiment according to FIG. 1 of a treatment arrangement, which is connected to a modified voltage supply device;

FIG. 7—shows a top view of a third embodiment of a treatment arrangement according to the invention, which is connected to a pole of a high-voltage supply device;

FIG. 8—shows a section through the treatment arrangement according to FIG. 7;

FIGS. 1 and 2 illustrate a treatment arrangement, in which a dielectric shielding layer 1, in which an electrode arrangement 2 is embedded such that the shielding layer 1 encloses the electrode arrangement 2 on all sides. For this purpose, the shielding layer 1 is formed having a thickness such that the electrode arrangement 2 is enclosed on all sides with a sufficiently thick dielectric shield, which prevents a noticeable current flow. The shielding layer 1 forms a lateral terminal tongue 3, into which the electrode arrangement 2 extends.

As may be seen from FIG. 4 in particular, the electrode arrangement 2 has two electrode strips 4, which extend parallel to one another as strip-shaped conductors and are wound in spirals in an oval shape, wherein inner ends 5 are terminated in linear pieces pointing antiparallel in one loop of the other electrode strip in each case. The two electrode strips extend parallel to one another in the terminal tongue 3 and end in contact surfaces 6, which are each connected via connecting lines 7 to one pole 8 of a high-voltage supply device 9. FIG. 1 schematically shows that an AC t) voltage is applied to one pole, which oscillates around a ground potential, while the other pole 8 is at the ground potential. The electrode arrangement 2 is thus supplied with an alternating AC high voltage. The two electrode strips 4 are arranged such that they always alternate sections extending in parallel with one another, and therefore the alternating high voltage of the high-voltage supply device 9 is always applied between the sections of the electrode strips lying parallel to one another and generates local electrical fields there, which are suitable for forming a dielectric barrier plasma.

Figure 4:
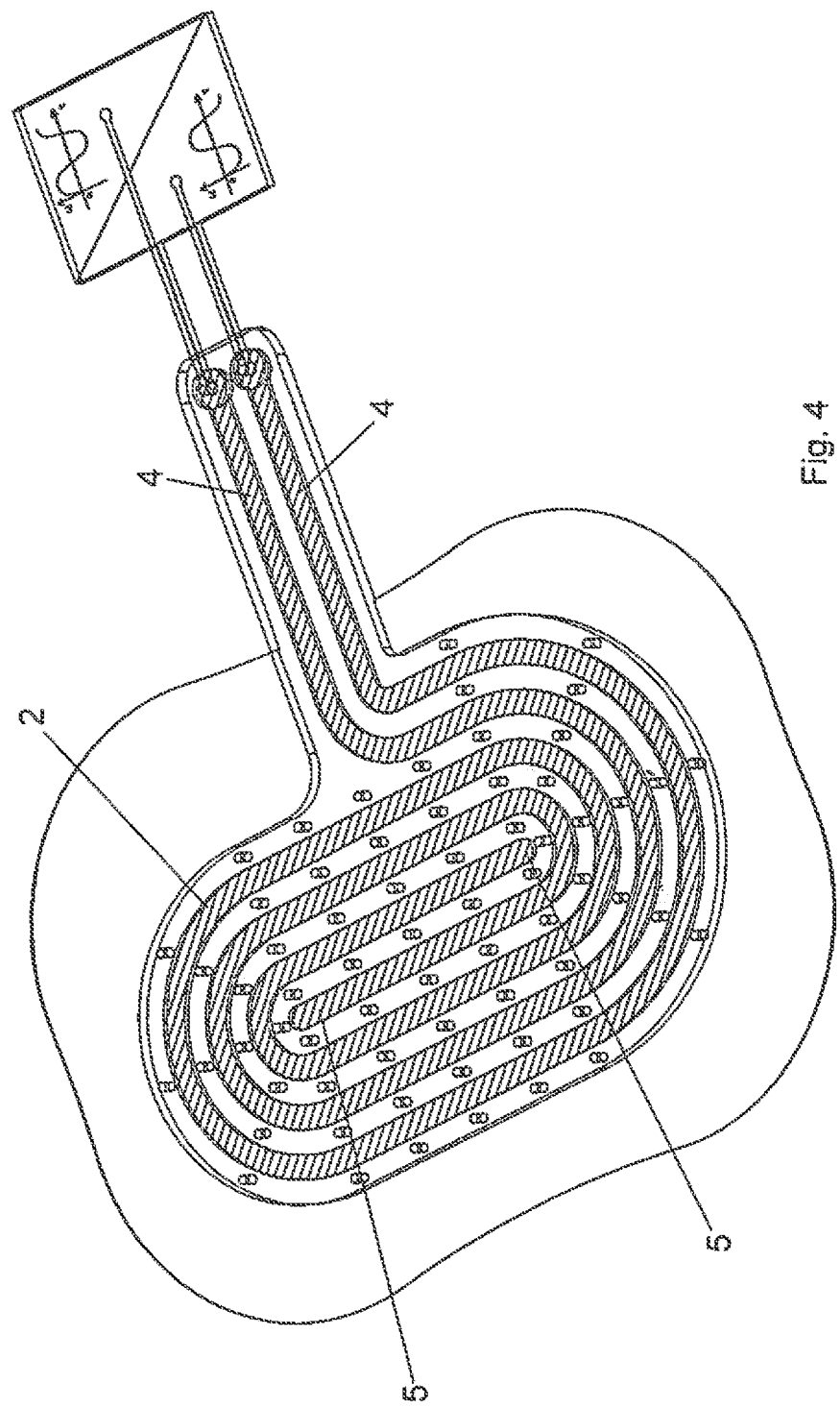
FIG. 4—shows the arrangement according to FIG. 3 in an illustration to show the electrode arrangement.

The dielectric shielding layer 1 is provided in one piece with sections 10, which extend on all sides with the exception of the terminal tongue 3 beyond the electrode arrangement 2 and the shielding layer 1 embedding the electrode arrangement 2 and are formed adhesive on the lower side 11 thereof, such that the treatment arrangement can be fastened on the skin of a body part like a self-adhesive bandage using the sections 10 which are adhesive on the lower side 11.

FIG. 2 illustrates the lesser thickness of the sections 10 in relation to the remaining shielding section 1, which embeds the electrode arrangement 2 in the form of the electrode strips 4 on all sides.

It may also be seen from FIGS. 1 and 2 that the dielectric shielding layer 1 is provided outside the electrode strips 4 with passage openings 12, via which air can reach a wound surface, on the one hand, and wound secretions are transportable from a wound surface from the lower side of the shielding layer 1 forming a treatment side 13 to the distally located upper side 14, on the other hand.

DETAILED DESCRIPTION

As FIG. 1 illustrates, the passage openings are located in the intermediate spaces between the electrode strips 4, and therefore the insulation of the electrode arrangement 2 is not endangered by the passage openings.

It may additionally be seen from FIG. 2 that the electrode arrangement 2 is a planar arrangement having a low height extension, which is formed in this embodiment of the invention by the planar electrode strips. These are preferably formed from a silicone which is electrically conductive due to conductive additives, which corresponds to the silicone of which the dielectric shielding layer 1 consists.

FIG. 3 merely shows that the two poles 8 of the high-voltage supply device can both be connected to alternating AC voltages, which have a phase shift of 180° in relation to one another, and therefore the resulting voltage difference for forming the local electrical fields between the electrode strips 4 has a double amplitude.

Figures 5, 6:
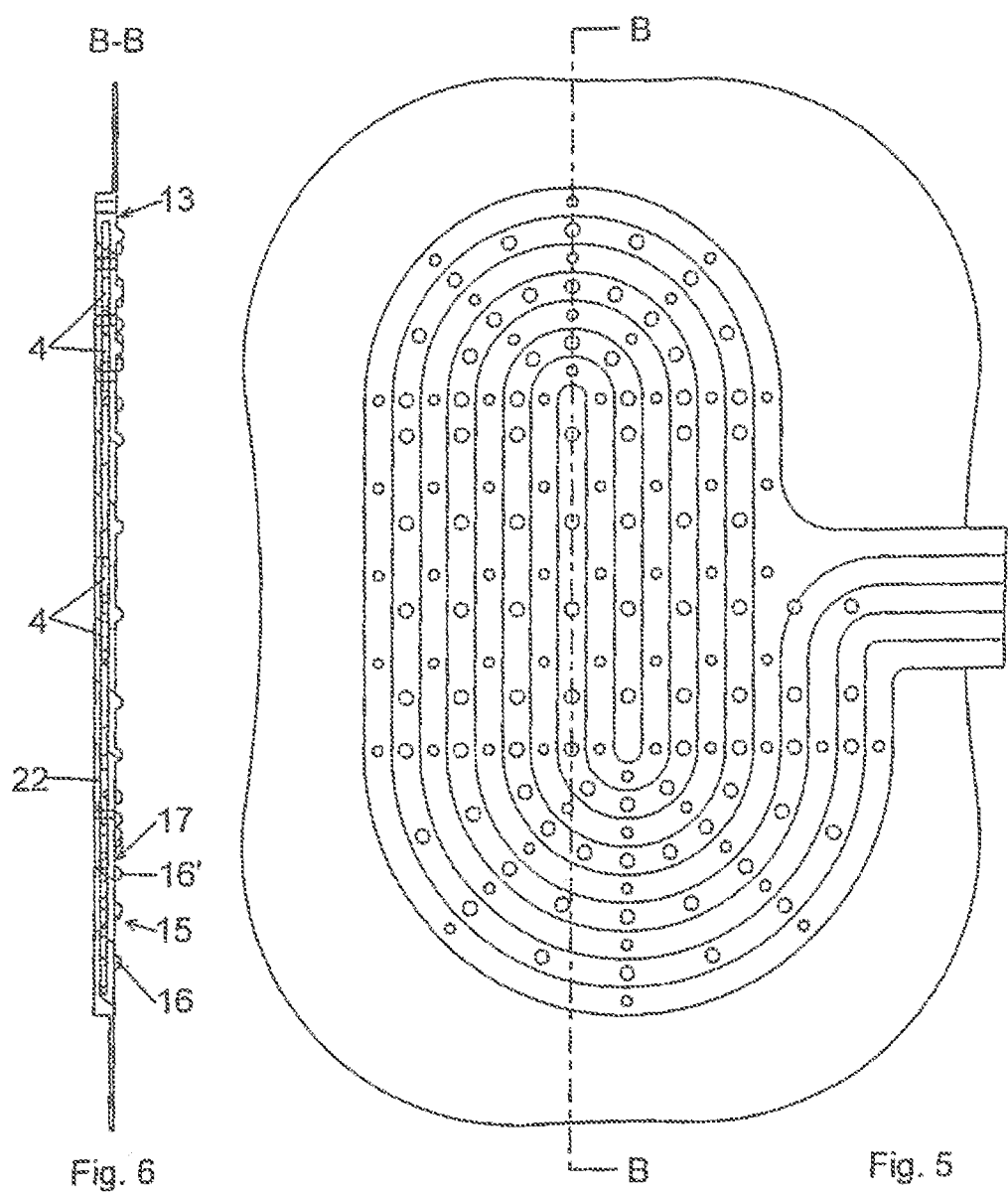
FIG. 5—shows a top view of a second exemplary embodiment of a treatment arrangement according to the invention.
FIG. 6—shows a section through the treatment arrangement according to FIG. 5 along line B-B.

The second exemplary embodiment illustrated in FIGS. 5 and 6 differs from the first exemplary embodiment according to FIGS. 1 to 4 solely in that the treatment side 13 of the dielectric shielding layer 1 is not formed smooth, but rather has a profile 15 in the form of hemispherical protrusions, with the upper sides of which the treatment arrangement can rest on the surface to be treated, i.e., in particular on the skin of a body part. Air intermediate spaces 17 are located between the application faces 16', in which air intermediate spaces a plasma can form due to the electrical fields built up between the electrode strips 4 when the treatment arrangement rests on the skin of a body part.

Figure 9:
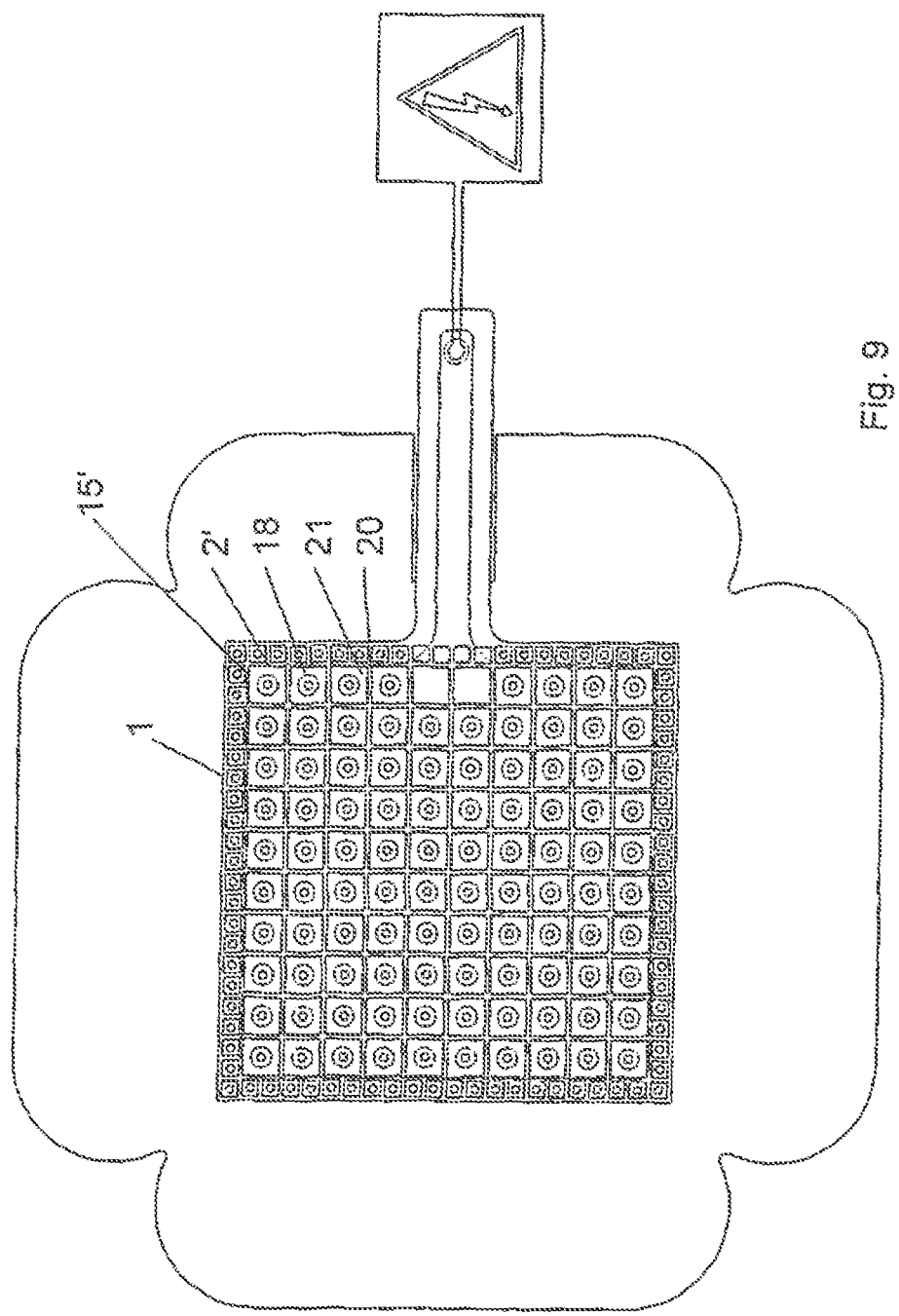
FIG. 9—shows a view from below of the treatment arrangement according to FIG. 7.

The exemplary embodiment illustrated in FIGS. 7 to 9 has a substantially square surface of the dielectric shielding layer 1, which is adjoined by integral sections 10' in a cloverleaf shape. The electrode arrangement 2' is formed by a continuous electrically conductive surface, in which circular passage openings 18 are located. The electrically conductive surface of the electrode arrangement 2' is embedded on all sides in the dielectric shielding layer 1. Passage openings 12 of the dielectric shielding layer, the diameter of which is significantly smaller than the diameter of the passage openings 18 in the electrode arrangement 2', however, extend concentrically with the passage openings 18. It is thus ensured that even in the region of the passage openings 12, which ensure a ventilation of the wound surface and a removal of wound secretions, a sufficient insulation in relation to the electrode arrangement 2' is always provided. The dielectric shielding layer 1 according to this exemplary embodiment also has a terminal tongue 3', into which a corresponding attachment of the electrode arrangement 2' extends, wherein the electrode arrangement 2' is also completely shielded on all sides by the dielectric shielding layer 1 in the region of the terminal tongue 3'. Contacting takes place via a contact point 19, via which a high-voltage potential of the high-voltage supply device 9 is conducted to the electrode arrangement 2'. In this embodiment, the body of the surface to be treated forms a counter electrode for the AC high voltage of the high-voltage supply device 9.

The view from below according to FIG. 9 illustrates a profile 15' of the treatment side 13 of the dielectric shielding layer 1. The profile 15' is formed with walls 20 aligned in a grid, which form chambers 21 (FIG. 8) open to the surface to be treated around the passage openings 12, 18, in which, as in the air intermediate spaces 17 of the preceding embodiments, a plasma can form when the treatment arrangement rests on the skin or wound surface of a body.

As FIGS. 6 and 8 illustrate, a boundary layer 22, via which the materials of the electrode arrangements 2, 2' and the shielding layers 1 are connected to one another by material-to-material joint according to the invention, exists in each case between the electrode arrangements 2, 2' and the dielectric shielding layers 1 enclosing them. It can be advantageous if the electrode arrangements 2, 2' and the shielding layers 1 consist of plastics which are substantially chemically equivalent, such as so-called liquid silicone rubbers or silicone gels. These plastic materials are insulating as a plastic matrix. For the electrode arrangements 2, 2', conductive additives are admixed to the insulating plastic material, and therefore the required conductive formation of the electrode arrangements 2, 2' is enabled in spite of the use of the insulating plastic matrix. In this manner, a bond which is secure against delamination even in the event of strong deformations of the flexible treatment arrangement is achieved between the electrode arrangement 2, 2' and the dielectric shielding layer 1.

However, it is also possible to use various plastics for the electrode arrangements 2, 2' and the shielding layers 1 in the scope of the invention, which may be crosslinked with one another either directly with one another or via a secondary crosslinking in the region of the boundary layer 22.

The invention claimed is:

1. A treatment arrangement for treating a surface, comprising:
   a planar electrode arrangement to which an electric voltage can be supplied;
   a planar shielding layer comprising an insulating plastic which at least partially encloses the electrode arrangement; and
   a boundary layer between the electrode arrangement and the shielding layer,
   wherein the electrode arrangement is formed from a pourable plastic with conductive additives,
   wherein in a region of the boundary layer between the electrode arrangement and the shielding layer, the plastic of the electrode arrangement and the insulating plastic of the shielding layer are connected to one another without an additional adhesive layer by the plastic of the electrode and the insulating plastic being mixed and/or cross-linked with one another in the region of the boundary layer.

2. The treatment arrangement as claimed in claim 1, wherein the electrode arrangement is enclosed on all sides by the shielding layer.

3. The treatment arrangement as claimed in claim 1, further comprising at least one electrically conductive terminal of the electrode arrangement which is led out of the shielding layer.

4. The treatment arrangement as claimed in claim 1, further comprising a contact arrangement for supplying the electrical voltage which is led through the shielding layer to the electrode arrangement.

5. The treatment arrangement as claimed in claim 1 wherein the shielding layer is profiled on a treatment side so as to form application surfaces between which air intermediate spaces for forming a plasma exist upon abutment of the treatment side of the treatment arrangement to a surface to be treated.

6. The treatment arrangement as claimed in claim 1 further comprising a wound dressing surface formed on a treatment side of the treatment arrangement.

7. The treatment arrangement as claimed in claim 1 wherein the plastic of the electrode arrangement and the insulating plastic of the shielding layer are chemically identical.

8. The treatment arrangement as claimed in claim 1 wherein the plastic of the electrode arrangement and the insulating plastic of the shielding layer are both silicones.

9. The treatment arrangement as claimed in claim 1 wherein the shielding layer has sections protruding beyond a surface of the electrode arrangement, wherein the sections are formed to be adhesive toward a surface to be treated.

10. The treatment arrangement as claimed in claim 1 wherein the electrode arrangement is configured to be connectable to a pole of the electric voltage and is designed such that a surface to be treated functions as a counter electrode.

11. The treatment arrangement as claimed in claim 1 wherein the electrode arrangement has two electrode strips which are configured to be connectable to two voltage-conducting poles of the electric voltage.

12. The treatment arrangement as claimed in claim 1 wherein the plastic of the electrode arrangement and the insulating plastic of the shielding layer are miscible with one another in a liquid state.

13. The treatment arrangement as claimed in claim 1 wherein the plastic of the electrode arrangement and the insulating plastic of the shielding layer are crosslinked with one another in the region of the boundary layer.

14. A treatment device comprising:
   a treatment arrangement as claimed in claim 1; and
   a high-voltage supply device connected to the electrode arrangement to form a plasma between a planar treatment side of the treatment arrangement and a surface to be treated.

15. A method for producing a treatment arrangement as claimed in claim 1 comprising:
   mixing with one another and in the liquid state at least in the region of the boundary surface between the electrode arrangement and the shielding layer the plastic of the electrode arrangement and the insulating plastic of the shielding layer; and
   jointly curing and/or crosslinking the plastic of the electrode arrangement and the insulating plastic of the shielding layer.

16. The method as claimed in claim 15, wherein at least one layer of the shielding layer and the plastic of the electrode arrangement are provided with the conductive additives in a liquid state and are introduced into a casting mold, and wherein the mixing step results in the boundary region between the plastic of the electrode arrangement and the insulating plastic of the shielding layer, and wherein mixing step is performed prior to the jointly curing and/or crosslinking.

17. The method as claimed in claim 15, wherein one of the plastic of the electrode arrangement and the insulating plastic of the shielding layer is partially crosslinked, and wherein in the mixing step is performed such that another of the plastic of the electrode arrangement and the insulating plastic of the shielding layer is subsequently conducted onto the partially crosslinked one of the plastic of the electrode arrangement and the insulating plastic of the shielding layer in the non-crosslinked state and a further crosslinking of the partially crosslinked one of the plastic of the electrode arrangement and the insulating plastic of the shielding layer is carried out with crosslinking to the another of the plastic of the electrode arrangement and the insulating plastic of the shielding layer.

18. The method as claimed in claim 15, wherein one of the plastic of the electrode arrangement and the insulating plastic of the shielding layer has crosslinkable functional groups in a crosslinked state, and wherein the material-to-material joint is produced with another of the plastic of the electrode arrangement and the insulating plastic of the shielding layer by a secondary crosslinking using the crosslinkable functional groups.

\* \* \* \* \*